(12) United States Patent
de Sousa (10) Patent No.: US 7,354,731 B2
(45) Date of Patent: Apr. 8, 2008

(54) METHOD OF SCREENING FOR POTENTIAL ANTI-BACTERIAL AGENTS

(75) Inventor: Sunita Maria de Sousa, Bangalore (IN)

(73) Assignee: AstraZeneca AB, Sodertalje (SE)

( * ) Notice: Subject to any disclaimer, the term of this patent is extended or adjusted under 35 U.S.C. 154(b) by 289 days.

(21) Appl. No.: 10/497,745

(22) PCT Filed: Dec. 3, 2002

(86) PCT No.: PCT/GB02/05492

§ 371 (c)(1),
(2), (4) Date: Nov. 15, 2004

(87) PCT Pub. No.: WO03/048380

PCT Pub. Date: Jun. 12, 2003

(65) Prior Publication Data

US 2005/0106555 A1    May 19, 2005

(30) Foreign Application Priority Data

Dec. 5, 2001    (SE) .................................... 0104102

(51) Int. Cl.
*C12Q 1/48*    (2006.01)
(52) U.S. Cl. ................................ 435/15; 435/4; 435/32
(58) Field of Classification Search .................... 435/4, 435/32, 15
See application file for complete search history.

(56) References Cited

U.S. PATENT DOCUMENTS

| | | | |
|---|---|---|---|
| 6,537,770 B1 * | 3/2003 | Das et al. ...................... | 435/24 |
| 6,913,895 B1 * | 7/2005 | Goldman et al. .......... | 435/7.32 |
| 6,955,886 B1 * | 10/2005 | Desousa et al. .............. | 435/7.2 |
| 2003/0129683 A1 * | 7/2003 | Kahne ......................... | 435/15 |
| 2006/0228766 A1 * | 10/2006 | Desousa et al. .............. | 435/15 |

FOREIGN PATENT DOCUMENTS

| | | |
|---|---|---|
| EP | 0 154 734 | 8/1990 |
| EP | 0 378 059 | 9/1993 |
| WO | WO-96/16082 | 5/1996 |
| WO | WO 96/16082 A1 * | 5/1996 |
| WO | WO-99/38958 | 8/1999 |
| WO | WO-99/60155 | 11/1999 |
| WO | WO 99/60155 A1 * | 11/1999 |
| WO | WO-00/10587 | 3/2000 |
| WO | WO-00/52035 | 9/2000 |
| WO | WO-01/12142 | 2/2001 |
| WO | WO-01/94622 | 12/2001 |
| WO | WO 01/94622 A1 * | 12/2001 |
| WO | WO-01/94623 | 12/2001 |
| WO | WO 01/94623 A1 * | 12/2001 |

OTHER PUBLICATIONS

Chandrakala B. et al. Novel Scintillation Proximity Assay for Measuring Membrane Associated Steps of Peptidoglycan Biosynthesis in *E. coli*. Antimicrobial Agents and Chemotherapy. Mar. 2001 45(3)768-775.*

Chandrakala B. et al. High Throuput Screen for Inhibitors of Transglycosylase and/or Transpeptidase Activities of *E. coli* Pencillin Binding Protein 1b. Antimicrobial Agents and Chemotherapy. Jan. 2004 48(1)30-40.*

Chandrakala B. et al. Assay for Inhibitors of the Transglycosylase and Transpeptidase Activities of the Penicillin Binding Protein. Antimicrobial Agents and Chemotherapy, Abstracts of the Interscience Conference Sep. 27-30, 2002. 2002, vol. 42, p. 191 F-718 abstract.*

Barbosa, M.D.F., et al., "Development of a Pathway Assay to Screen for Bacterial Cell Wall Biosynthesis Inhibitors," 41:248 (2001) XP009010101.

Boyle, D.S., et al., "mraY is an Essential Gene for Cell Growth in *Escherichia coli*," Journal of Bacteriology, 180(23):6429-6432 (1998).

Branstrom, A.A., et al., "In situ assay for identifying inhibitors of bacterial transglycosylase," FEMS Microbiology Letters, 191: 187-190 (2000).

Chandrakala, B., et al., "Novel Scintillation Proximity Assay for Measuring Membrane-Associated Steps of Peptidoglycan Biosynthesis in *Escherchia coli*," Antimicrobial Agents and Chemotherapy, 45(3):768-775 (2001).

dem Blaauwen, T., et al., "Interaction of Monoclonal Antibodies with the Enzymatic Domains of Penicillin-Binding Protein 1b of *Escherichia coli*," Journal of Bacteriology, 172(1):63-70 (1990).

Denome, S.A., et al., "*Escherichia coli* Mutants Lacking All Possible Combinations of Eight Penicillin Binding Proteins: Viability, Characteristics, and Implications for Peptidoglycan Synthesis," Journal of Bacteriology, 181(13):3981-3993 (1999).

Ge, M., et al., "Vancomycin Derivatives That Inhibit Peptidoglycan Biosynthesis Without Binding D-Ala-D-Ala," Science, 284:507-511 (1999).

(Continued)

*Primary Examiner*—Ralph Gitomer (57) ABSTRACT

The invention provides a method of screening for potential anti-bacterial agents being antagonists of one or both of the transglycosylase and the transpeptidase enzymes involved in peptidoglycan biosynthesis in bacteria. The method is suitable for high throughput screening of compounds.

8 Claims, 5 Drawing Sheets

OTHER PUBLICATIONS

Goldman, R.C., et al., "Chlorobiphenyl-deseucyl-vancomycin inhibits the transglycosylation process required for peptidoglycan synthesis in bacteria in the absence of dipeptide binding," FEMS Microbiology Letters, 183:209-214 (2000).

Lefevre, F., "Topographical and Functional Investigation of *Escherichia coli* Penicillin-Binding Protein 1b by Alanine Stretch Scanning Mutagenesis," Journal of Bacteriology, 179(15):4761-4767 (1997).

Lo, M.C., et al., "A New Mechanism of Action Proposed for Ramoplanin," J. Am. Chem. Soc., 122:3540-3541 (2000).

Mengin-Lecreuix, D., et al., "The murG Gene of *Escherichia coli* Codes for the UDP-N-Acetylglucosamine:N-Acetylmuramyl-(Pentapeptide) Pyrophosphoryl-Undecaprenol N-Acetylglucosamine Transferase Involved in the Membrane Steps of Peptidoglycan Synthesis," 173(15):4625-4636 (1991).

Pinho, M.G., et al., "An acquired and a native penicillin-binding protein cooperate in building the cell wall of drug-resistant staphylococci," PNAS, 98(19): 10886-10891 (2001).

Tamura, T., et al., "On the process of cellular division in *Escherichia coli*: Isolation and characterization of penicillin-binding proteins 1a, 1b, and 3," Proc. Natl. Acad. Sci. USA, 77(8):4499-4503 (1980).

van Heijenoort, Y., et al., "Membrane Intermediates in the Peptidoglycan Metabolism of *Escherichia coli*: Possible Roles of PBP 1b of PBP 3," Journal of Bacteriology, 174(11):3549-3557 (1992).

Yousif, S.Y., "Lysis of *Escherichia coli* by β-Lactam Antibiotics: Deletion Analysis of the Role of Penicillin-binding Proteins 1A and 1B," Journal of General Microbiology, 131:2839-2845 (1985).

\* cited by examiner

METHOD OF SCREENING FOR POTENTIAL ANTI-BACTERIAL AGENTS

CROSS-REFERENCE TO RELATED APPLICATIONS

This application is a national stage filing under 35 U.S.C. 371 of International Application No. PCT/GB02/05492, filed Dec. 3, 2002, which claims priority from Swedish Patent Application No. 0104102-9, filed Dec. 5, 2001, the specification of which is incorporated by reference herein. International Application No. PCT/GB02/05492 was published under PCT Article 21(2) in English.

The present invention relates to a method of screening for potential anti-bacterial agents.

Peptidoglycan is a major component of the bacterial cell wall that gives the wall its shape and strength. It is unique to bacteria and is found in all bacteria, both gram-positive and gram-negative. Peptidoglycan is a polymer of glycan strands that are cross-linked through short peptide bridges. It consists of alternating β1-4 linked residues of N-acetyl glucosamine (GlcNAc) and N-acetyl muramic acid (MurNAc). A pentapeptide chain is attached to MurNAc (MurNAc-pentapeptide) and cross-linking occurs between these peptide chains.

Biosynthesis of peptidoglycan can be divided into three stages: firstly, synthesis of the precursors in the cytoplasm, secondly, transfer of the precursors to a lipid carrier molecule and, thirdly, insertion of the precursors into the cell wall and coupling to existing peptidoglycan.

The precursors synthesised in the cytoplasm are the sugar nucleotides: UDP-N-acetyl-glucosamine (UDP-GlcNAc) and UDP-N-acetylmuramylpentapeptide (UDP-MurNAc-pentapeptide).

The second stage, which occurs in the cytoplasmic membrane, is catalysed by two enzymes and involves synthesis of a disaccharide unit on a lipid carrier, undecaprenyl phosphate. The lipid carrier is also involved in the synthesis of other components of the bacterial cell wall.

The first enzyme catalyses the transfer of phosphoryl-N-acetyl muramyl pentapeptide from UDP-MurNAc-pentapeptide to undecaprenyl phosphate with the simultaneous release of UMP. This enzyme is called phospho-N-acetyl-muramylpentapeptide translocase (hereafter referred to as "the translocase") and is the product of the gene mraY in *Escherichia coli*. The product, undecaprenyl-pyrophosphate-N-acetylmuramylpentapeptide (Lipid-P-P-MurNAc-pentapeptide) or Lipid I or Lipid linked precursor I is the substrate for the second enzyme.

N-acetylglucosaminyl transferase, transfers N-acetylglucosamine from UDP-GlcNAc (with simultaneous release of UDP) to form undecaprenyl-pyrophosphoryl-N-acetylmuramylpentapeptide-N-acetylglucosamine or Lipid II or Lipid linked precursor II. This enzyme is also called UDP-N-acetylglucosamine: N-acetylmuramyl(pentapeptide)-P-P-undecaprenyl-N-acetylglucosamine transferase (hereafter referred to as "the transferase"). The enzyme is the product of the gene murG in *Escherichia coli*.

The translocase and the transferase enzymes are essential for bacterial viability (see respectively D. S. Boyle and W. D. Donachie, *J. Bacteriol.*, (1998), 180, 6429-6432 and D. Mengin-Lecreulx, L. Texier, M. Rousseaue and Y. Van Heijernoot, *J. Bacteriol.*, (1991), 173, 4625-4636).

In the third stage, at the exterior of the cytoplasmic membrane, polymerisation of the glycan occurs. The disaccharide-pentapeptide unit is transferred from the lipid carrier to an existing disaccharide unit or polymer by a peptidoglycan transglycosylase (also referred to as a peptidoglycan polymerase) (hereafter referred to as "the transglycosylase"). The joining of the peptide bridge is catalyzed by peptidoglycan transpeptidase (hereafter referred to as "the transpeptidase"). Both enzyme activities which are essential reside in the same molecule, the penicillin binding proteins (or PBPs), as in PBP 1a or 1b in *Escherichia coli*. These are the products of the ponA and ponB genes respectively, in *Escherichia coli*.

There are several PBPs in the bacterial cell and these can be divided into two classes, the low molecular mass (LMM) and high molecular mass (HMM) PBPs. Some of the HMM PBPs are bifunctional enzymes having both transpeptidase and transglycosylase activity. Of the HMM PBPs, PBP2 and PBP3 and either PBP1A or PBP1B of *E. coli* have been shown to be essential for cell viability. The LMM PBPs appear to be important but not essential for cell growth (e.g. PBPs 4, 5, 6 of *E. coli* can be deleted resulting in growth defects but the cell survives, see S. A. Denome, P. K. Elf, T. A. Henderson, D. E. Nelson and K. D. Young, *J. Bacteriol.*, (1999), 181(13), 3981-3993).

On transfer of the disaccharide-pentapeptide unit from the lipid precursor to an existing peptidoglycan chain the lipid is released as a molecule of undecaprenyl pyrophosphate. This has to be cleaved by a bacitracin-sensitive undecaprenyl pyrophosphorylase, also called undecaprenyl pyrophosphorylase or C55-isoprenyl pyrophosphorylase (hereafter referred to as the "lipid pyrophosphorylase") to generate undecaprenyl phosphate which can then re-enter the cycle at the second stage.

Both the transglycosylase and the transpeptidase enzymes (which reside within the high molecular weight penicillin binding proteins or PBPs) represent prime targets for drug discovery that have not been fully exploited due to the lack of suitable assays amenable to high throughput screening. Two antibiotics target these proteins: the glycopeptides and the beta-lactam antibiotics-penicillins and cephalosporins. The beta-lactam antibiotics, which inhibit the transpeptidase, are one of the most successful and have yielded many generations of drugs. Vancomycin, a glycopeptide, is an inhibitor of the transglycosylase and in many cases of drug resistance is the last resort for treatment of bacterial infections. It is thus thought that new inhibitors of the transglycosylase and transpeptidase will be as successful and could become clinically useful antibiotics.

A conventional enzyme assay for the transglycosylase involves using radiolabelled Lipid II as substrate and monitoring incorporation of the radiolabel into peptidoglycan which is monitored by paper chromatography. In the paper chromatogram, peptidoglycan stays at the origin whereas the substrate, Lipid II, runs with an Rf of ~0.9. However, the substrate for the transglycosylase, Lipid II, is very hard to isolate in quantities sufficient for high throughput assays; it is usually made by isolating Lipid I and incubating it with a source of transferase in the presence of radiolabelled UDP-GlcNAc so as to make radiolabelled Lipid II. In addition, the Lipid II is not water-soluble and reactions do not often take place in the solution phase but are carried out on Whatman 3 mm paper. This makes the reaction conditions hard to control. Since the product of the enzymatic reaction has to be analysed by paper chromatography it is not suitable for high throughput screening.

An assay for the transglycosylase enzyme has recently been described by Mei-Chu Lo et al in *J. Am. Chem. Soc.*, (2000), 122, 3540-3541, where Lipid II is made by incubating *E. coli* membranes with UDP-MurNAc-pentapeptide and radiolabelled UDP-GlcNAc in the presence of the detergent, Triton X-100, which is an inhibitor of the transglycosylase. In a subsequent step the Triton X-100 is removed by the addition of beads to allow the transglycosylase reaction to proceed. The removal of the Triton X-100 by beads is tedious and also subsequent analysis by paper chromatography or by filtration makes it inconvenient for screening large numbers of test compounds.

WO 00/52035 describes a high througput assay for the transglycosylase enzyme which is said to overcome the problems of the earlier methods (such as the difficulties of obtaining large quantities of Lipid II from natural sources and its handleability, e.g. being water-insoluble, as well as the use of paper chromatography). The assay relies on the use of chemically modified analogues of Lipid I and/or Lipid II (i.e. artificial substrates). The synthesis of artificial substrates does not necessarily make for an efficient and cost effective assay for screening test compounds. Furthermore, all of the Examples in WO 00/52035 appear to be theoretical and there is no actual data to support the suitability of the assay for high throughput screening. Indeed, the only assay that appears to have been carried out, the results of which are shown in FIG. 7 of WO 00/52035, was one in which the product obtained was detected by paper chromatography.

It would be desirable to develop a method for assaying the activity of one or both of the transglycosylase and transpeptidase enzymes which is suitable for high throughput screening.

In accordance with the present invention, there is therefore provided a method of screening for potential antibacterial agents which comprises:

(1) providing a membrane preparation obtained from a bacterial strain which may be deficient for peptidoglycan transglycosylase activity;

(2) preparing a reaction mixture comprising the membrane preparation, a UDP-N-acetylmuramylpentapeptide (UDP-MurNAc-pentapeptide), radiolabelled UDP-N-acetyl glucosamine (UDP-GlcNAc), a source of divalent metal ions and, optionally, an inhibitor effective to inhibit further processing of undecaprenyl-pyrophosphoryl-N-acetylmuramylpentapeptide-N-acetylglucosamine (Lipid II);

(3) incubating the reaction mixture for a defined period under conditions suitable for Lipid II synthesis to occur;

(4) adding to the reaction mixture of step (3),
  (a) either a substance to neutralise the inhibitor, or a source of peptidoglycan transglycosylase and a source of peptidoglycan transpeptidase, to allow further processing of Lipid II formed in step (3) toward peptidoglycan, and
  (b) a test compound;

(5) after a defined period, terminating any further processing of Lipid II;

(6) adding to the reaction mixture of step (5) a fluorescer supported by, in or on a suitable substrate, and a detergent; and (7) measuring light energy emitted by the fluorescer which is indicative of the presence of radiolabelled peptidoglycan.

In the context of the present specification, it should be understood that the abbreviation "UDP" refers to uridine (5'-)diphosphate.

The method according to the present invention is very conveniently carried out using 96-well microtitre plates, thereby enabling a fast, simple and reproducible way of measuring enzyme activity.

The bacterial membranes may be prepared as described in Example 1 of WO 99/60155. The membranes represent, inter alia, a source of undecaprenyl phosphate, a source of translocase enzyme and a source of transferase enzyme which are required to make Lipid II.

The quantity of membranes used will typically be in the range from 1 to 20 µg, particularly from 4 to 6 µg, protein per well of the microtitre plate.

Up until the end of step (3) of the method, peptidoglycan synthesis proceeds as far as the formation of Lipid II which is allowed to build-up in the reaction mixture. This build-up of Lipid II can be achieved in several ways which include the use of an inhibitor effective to inhibit further processing of Lipid II (for example, an inhibitor of the transglycosylase enzyme such as vancomycin or moenomycin if the membrane preparation contains this enzyme); the use of membranes from a bacterial strain that is deficient for the transglycosylase enzyme activity (for example, as described in WO 96/16082); and the use of membranes prepared by a method involving treating bacterial cells firstly with lysozyme (for example, as described by Y. van Heijenoort et al., (1992), *J. Bacteriol.*, 174, 3549-3557).

In one embodiment of the invention, the membranes of *Escherichia coli* bacteria are used. Examples of *E. coli* strains that may be used include AMA1004 and AMA1004 ΔponB::Spc$^r$ (in which the gene ponB encoding PBP1b has been inactivated) as well as strains derived from the latter that have been transformed with an expression vector (e.g. a plasmid) comprising a homologous or heterologous gene encoding a penicillin binding protein.

The *E. coli* (mutant) strain AMA1004 ΔponB::Spc$^r$ is viable because of the presence of the ponA gene which encodes PBP1a having transglycosylase and transpeptidase activities. However, when using membranes from this strain, it is not necessary, for example, to employ an inhibitor of Lipid II further processing because it has been observed that, in vitro, under the assay conditions described here, PBP1a behaves as if it has no transglycosylase or transpeptidase activity.

Transformation of the above mutant strain with an expression vector containing a gene encoding a penicillin binding protein serves to counteract the transglycosylase deficiency of the mutant strain and thus build-up of Lipid II in step (3) of the method will require, for example, the presence of an inhibitor effective to inhibit further processing of Lipid II.

Transformed mutants are particularly advantageous if it is desired to screen compounds against a heterologous penicillin binding protein which might be unstable, or susceptible to inactivation by detergent or perhaps difficult to solubilise under the conditions employed in the method of the invention. Examples of such penicillin binding proteins include those of *Mycobacterium leprae* and *Mycobacterium smegmatis*. Methods for preparing the transformed mutants are described in the literature (see, for example, T. Tamura et al., (1980), *Proc. Natl. Acad. Sci. USA,* 77(8), 4499-4503).

The UDP-MurNAc-pentapeptide used may be any of those usually present in naturally-occurring peptidoglycans and is conveniently purified from bacteria or made enzymatically with precursors from bacteria, e.g. by methods similar to that described by T. den Blaauwen, M. Aarsman and N. Nanninga, J. Bacteriol., (1990), 172, 63-70).

In one embodiment of the invention, the UDP-MurNAc-pentapeptide used is UDP-MurNAc-L-alanine-γ-D-glutamic acid-m-diaminopimelic acid-D-alanine-D-alanine from *Bacillus cereus*.

The concentration of UDP-MurNAc-pentapeptide used per well of microtitre plate will typically be in the range from 5 µM to 300 µM, for example, from 5 µM, 10 µM, 15 µM, 20 µM or 25 µM up to and including 50 µM, 75 µM, 100 µM, 150 µM, 200 µM or 250 µM per well of the microtitre plate.

As radiolabelled UDP-N-acetyl glucosamine, it is convenient to use tritiated UDP-N-acetyl glucosamine (UDP-[$^3$H] GlcNAc, commercially available from NEN-Dupont), at a concentration, for example, in the range from 0.25 µM, 0.5 µM, 1.0 µM, 2.5 µM, 4.2 µM or 5 µM up to and including 10 µM, 12.5 µM, 15 µM, 20 µM or 25 µM per well of the microtitre plate. Concentrations of radiolabelled UDP-N-acetyl glucosamine of 2.5 µM (with 0.1 to 0.5 µCi radioactivity per well) or 4.2 µM (with 0.6 to 1.2 µCi per well) have been advantageously used.

The divalent metal ions used are preferably magnesium ions. A suitable source of magnesium ions is magnesium chloride, for example at a concentration in the range from 5 to 30 mM, particularly from 10 to 25 mM, per well of microtitre plate.

The inhibitor effective to inhibit further processing of undecaprenyl-pyrophosphoryl-N-acetylmuramylpentapeptide-N-acetylglucosamine (Lipid II) may conveniently be selected from known inhibitors of the transglycosylase enzyme which include vancomycin, ristocetin, moenomycin, mersacidin and actagardine. The amount of inhibitor used will depend on the inhibitor chosen and, in those instances where the inhibitor is capable of inhibiting other enzymes involved in peptidoglycan synthesis, the amount of inhibitor used will be chosen such that the transglycosylase is selectively inhibited. For example, it has been found that vancomycin (which is capable of inhibiting the translocase and transferase enzymes in addition to the transglycosylase enzyme) may be advantageously used at a concentration in the range from 10 to 200 µM, particularly from 30 to 100 µM or from 40 to 60 µM, per well of microtitre plate to selectively inhibit the transglycosylase.

In step (2) of the method, it may be convenient to use an aqueous medium such as a buffer solution, e.g. of HEPES-ammonia, HEPES-KOH (HEPES being N-[2-hydroxyethyl]piperazine-N'-[2-ethanesulfonic acid]) or Tris[hydroxymethyl]aminomethane hydrochloride ("Tris-HCl"), the buffer solution having a pH of about 7.5. HEPES and Tris-HCl are commercially available from the Sigma-Aldrich Company Limited.

The reaction mixture prepared in step (2) is incubated in step (3) at a temperature in the range from, for example, 20° C. to 37° C. for a period in the range from, for example, 2, 3, 4, 5, 10, 20, 30, 40 or 50 minutes up to and including 100, 110, 120, 130, 140 or 150 minutes, under conditions suitable for enzyme-catalysed Lipid II synthesis to occur.

In step (4) of the invention, the conversion of Lipid II towards cross-linked peptidoglycan is initiated. If an inhibitor of Lipid II further processing is present in the reaction mixture, a substance is added in order to neutralise it and so make it ineffective. For example, if the inhibitor used is vancomycin, this may conveniently be achieved by adding a substance containing a terminal D-Ala-D-Ala dipeptide to which vancomycin is known to bind such as the tripeptide Lys-D-Ala-D-Ala or UDP-MurNAc-pentapeptide. The former is preferred since it is not also a reagent. The neutralising substance will conveniently be added as a molar excess (relative to the molar amount of inhibitor).

Alternatively, if there are no active or effective transglycosylase and transpeptidase enzymes present in the reaction mixture (as, for example, when using membranes from the above mutant strain of *E. coli*), then they will need to be added in step (4); this is further illustrated in the experimental section. For example, a purified homologous or heterologous penicillin binding protein containing both transglycosylase and transpeptidase activities, or a solubilised fraction of membranes (including those from a transformed mutant as described above) containing a protein(s) with transglycosylase and transpeptidase activities may be added.

In step (4), a test compound having potential antibacterial properties is added, typically in an aqueous solution of dimethyl sulphoxide.

The reaction mixture of step (4) is incubated for a further period at a temperature in the range from, for example, 20° C. to 37° C. The incubation period will normally be shorter than the incubation period for the reaction mixture of step (3), e.g. in the range from 1, 5 or 10 minutes up to and including 20, 25 or 30 minutes.

Once the incubation period has come to an end, any further processing of Lipid II is terminated in step (5). This may be achieved by any suitable means. In one embodiment of the invention, a suitable amount of a divalent metal ion chelator compound is added, e.g. ethylenediaminetetraacetic acid (EDTA) (commercially available from the Sigma-Aldrich Company Limited). The concentration of the chelator compound will of course depend on the particular chelator compound used. In the case of EDTA, the molar concentration will be at least half, preferably from 1.5 to 2 times, the molar concentration of divalent metal ions used.

In step (6), a fluorescer supported by, in or on a suitable substrate is added along with a detergent to the reaction mixture.

The detergent is any agent that is capable of emulsifying oil and/or acts as a wetting agent or surfactant. Examples of detergents that may be used include Triton X-100 (t-octylphenoxypolyethoxyethanol), Tween 20 (polyoxyethylenesorbitan monolaurate), Tween 80 (polyoxyethylenesorbitan monooleate), octyl-β-glycoside, CHAPS (3-[(3-cholamidopropyl)dimethylammonio]-1-propanesulphonate), Brij-35 (polyoxyethylene lauryl ether) and Sarkosyl (sodium lauryl sarcosinate).

The fluorescer used may be any of those routinely employed in scintillation proximity assays. The fluorescer is associated with or supported by, in or on a substrate, for example, lectin-coated beads, RNA-binding beads, anti-mouse antibody coated PVT (polyvinyltoluene) beads or wheatgerm agglutinin-coated PVT beads, all of which beads are commercially available from Amersham Inc. The substrate (e.g. beads) chosen should be capable of binding to bacterial cell walls.

In one embodiment of the invention, lectin-coated beads (particularly wheatgerm agglutinin-coated beads) impregnated with a fluorescer are used, for example, as described in U.S. Pat. No. 4,568,649 and European Patent No. 154, 734. The beads (known as "Scintillation Proximity Assay" (or SPA) beads) are commercially available from Amersham Inc.

The beads (with fluorescer), which are conveniently added in the form of an aqueous suspension, are contacted with the reaction mixture of step (5) for a period of at least 10 minutes, preferably 3 to 10 hours or more (e.g. overnight), before the plate is "counted" in step (7), e.g., in a "Microbeta Tilux" counter.

Without being bound to any particular theory, it is believed that through the binding of the substrate to bacterial cell wall material (e.g. wheatgerm agglutinin-coated SPA beads are capable of binding sugar molecules, specifically N-acetyl glucosamine, present in bacterial cell wall material), radiolabelled crosslinked peptidoglycan formed in step (4) is brought into close proximity with the fluorescer which becomes activated by the radiation energy, resulting in the emission of light energy which is measured in step (7). Thus, light emitted from the fluorescer is believed to be indicative of the formation of cross-linked peptidoglycan.

The present invention will now be further explained by reference to the following illustrative examples in which the abbreviation HEPES refers to N-[2-hydroxyethyl]piperazine-N'-[2-ethanesulfoni acid].

EXAMPLE 1

(i) Formation of Radiolabelled Lipid II

The wells of a microtitre plate were individually filled with 15 µl of a solution containing 4 µg of *Escherichia coli* AMA1004 cell membranes prepared as described in WO 99/60155 (the membranes provided a source of translocase, transferase, transglycosylase, transpeptidase, lipid pyrophosphorylase and undecaprenyl phosphate), 15 µM UDP-MurNAc-L-alanine-γ-D-glutamic acid-m-diaminopimelic acid-D-alanine-D-alanine, 4.2 µM tritiated UDP-N-acetyl glucosamine (0.6 µCi-1.2 µCi per well), 40 µM vancomycin (inhibitor of the transglycosylase), 50 mM HEPES-ammonia buffer pH 7.5, and 10 mM magnesium chloride ($MgCl_2$). The microtitre plate was incubated at 37° C. for 120 minutes.

(ii) Formation of Radiolabelled Peptidoglycan

To each well was then added 10 µl containing 50 mM HEPES-ammonia buffer pH 7.5, 10 mM $MgCl_2$, UDP-N-acetyl glucosamine to a final concentration (in 25 µl) of 250 µM, a tripeptide to neutralise the vancomycin inhibitor: Nα Nε, diacetyl-Lys-D-Ala-D-Ala to a final concentration of 400 µM (in 25 µl; available from Sigma-Aldrich Company Limited, catalogue number D-9904), and 2 µl of test compound (moenomycin, a known transglycosylase inhibitor) in dimethyl sulphoxide (DMSO). The microtitre plate was then incubated at 37° C. for 5 minutes and thereafter 75 µl of 6 mM ethylenediaminetetraacetic acid (EDTA) was added to stop any further peptidoglycan synthesis.

(iii) Detecting Radiolabelled Peptidoglycan

Following addition of the EDTA, there was added to each well 100 µl of an aqueous suspension of wheatgerm agglutinin-coated scintillation proximity assay beads comprising 500 µg beads in a solution of 50 mM HEPES-ammonia buffer pH 7.5 containing 0.4% "Sarkosyl" detergent (sodium lauryl sarcosinate) so that the final concentration of "Sarkosyl" detergent (in 200 µl) was 0.2%.

The microtitre plate was left for 3 to 10 hours at room temperature before being counted in the "Microbeta Trilux" counter.

Four wells of the microtitre plate were used as controls: two wells had EDTA and 10 µl water added at the end of (i) (0% reaction controls) and a further two wells contained no test compound (100% reaction controls).

Figure 1:
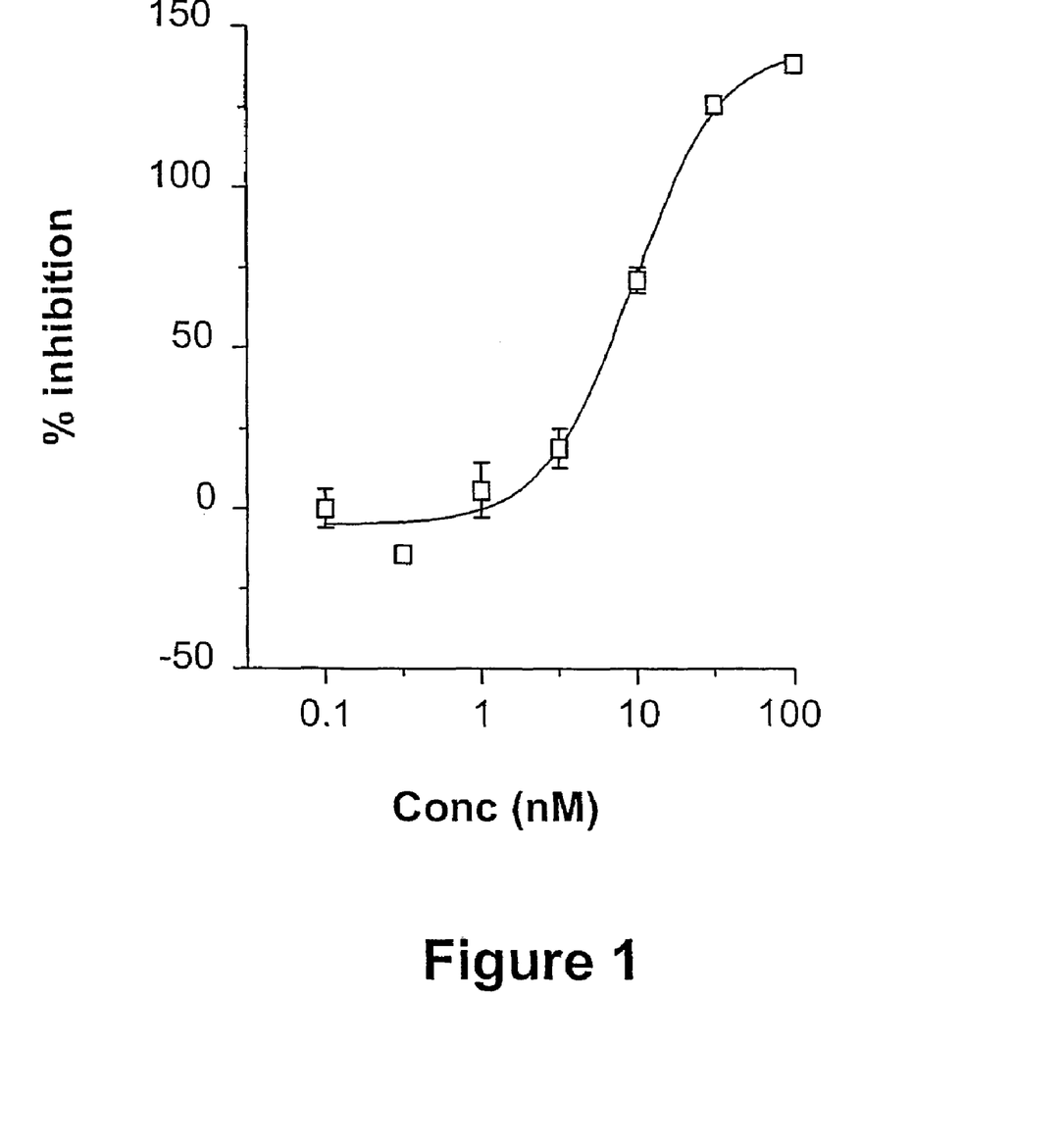
FIG. 1 is a graph showing the percentage inhibition of transglycosylase (and thus peptidoglycan synthesis) versus moenomycin concentration (after subtracting the corresponding 0% reaction readings).
Figure 2:
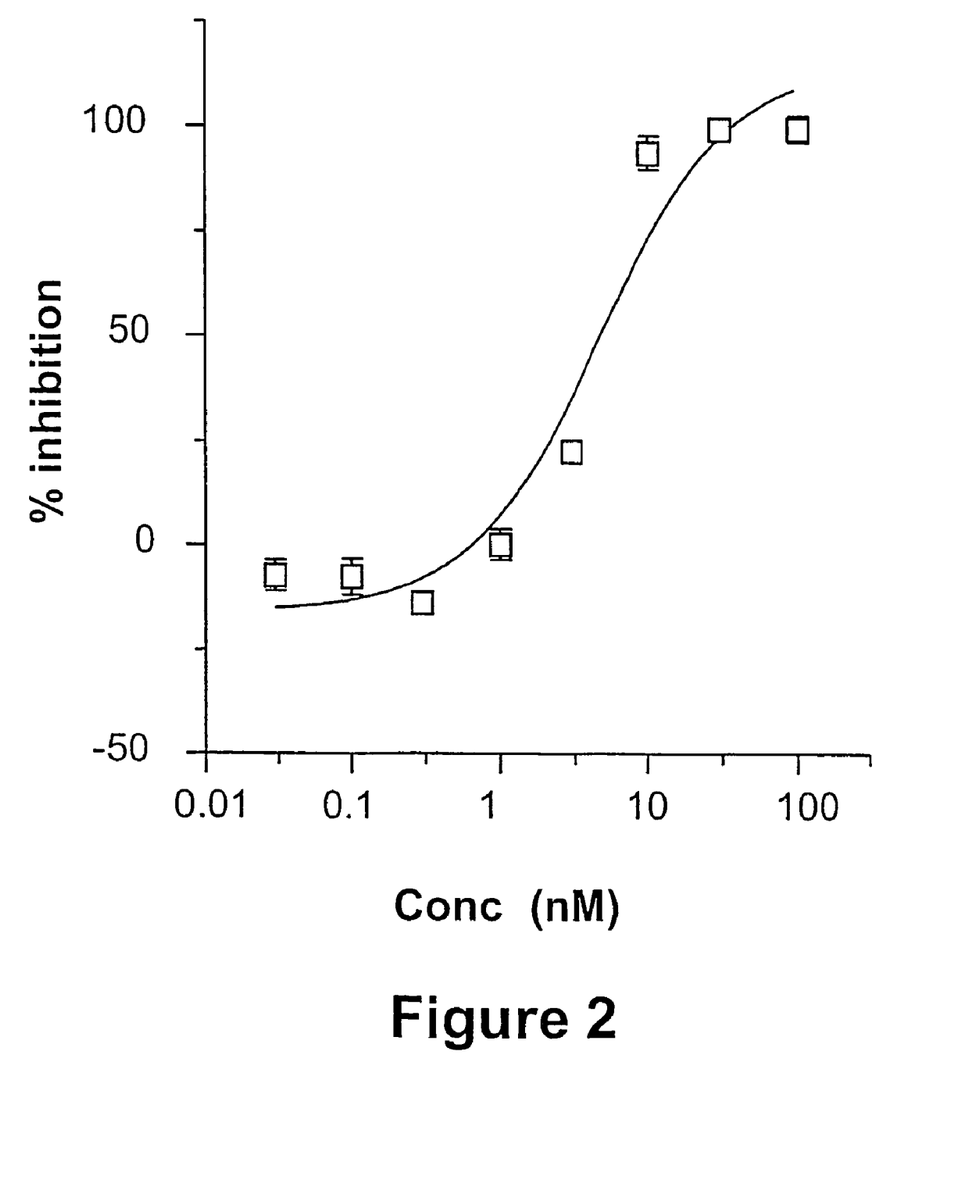
FIG. 2 is a graph showing the percentage inhibition of transglycosylase (and thus peptidoglycan synthesis) versus moenomycin concentration (after subtracting the corresponding 0% reaction readings).
Figure 3:
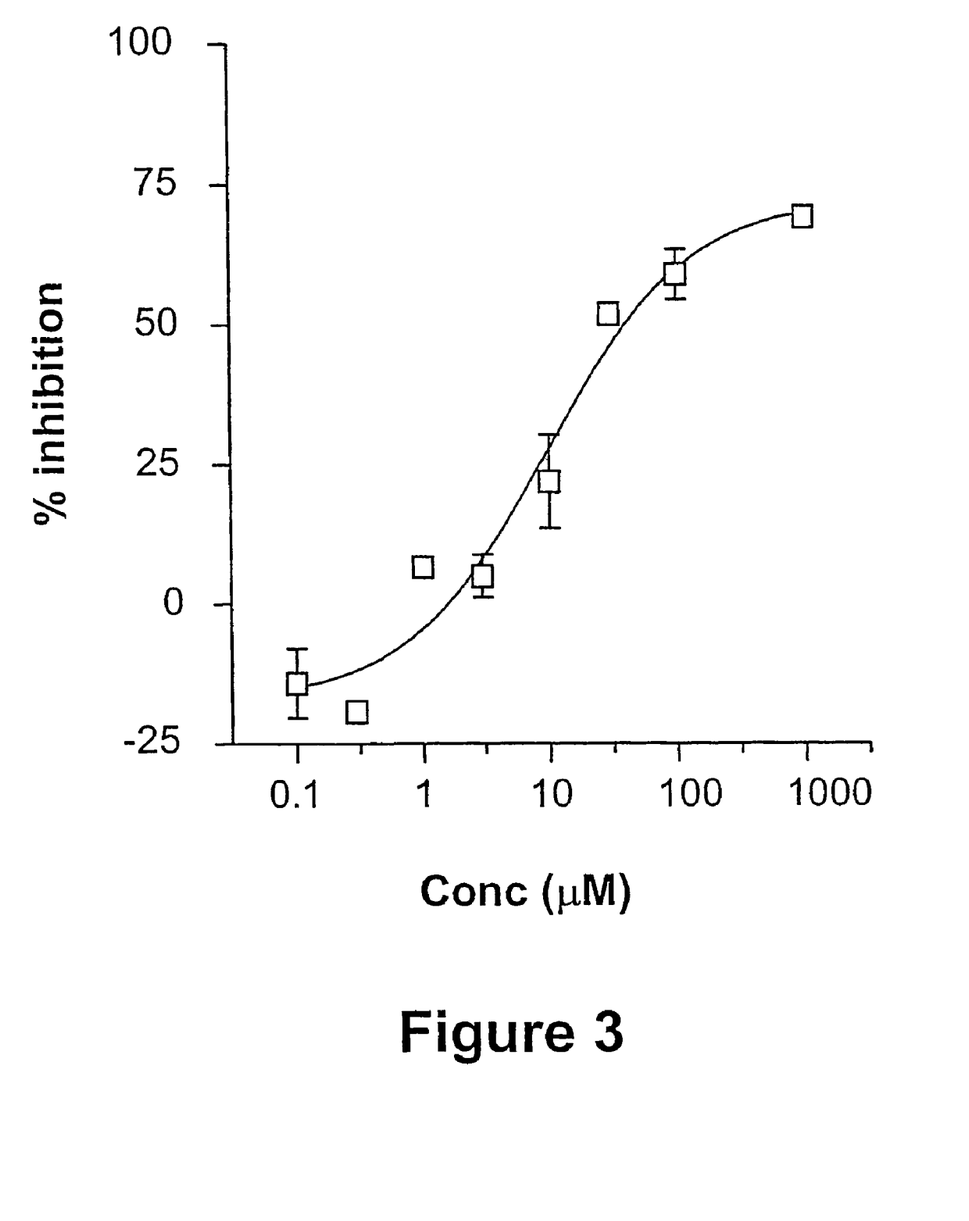
FIG. 3 is a graph showing the percentage inhibition of transglycosylase (and thus peptidoglycan synthesis) versus vancomycin concentration (after subtracting the corresponding 0% reaction readings).
Figure 4:
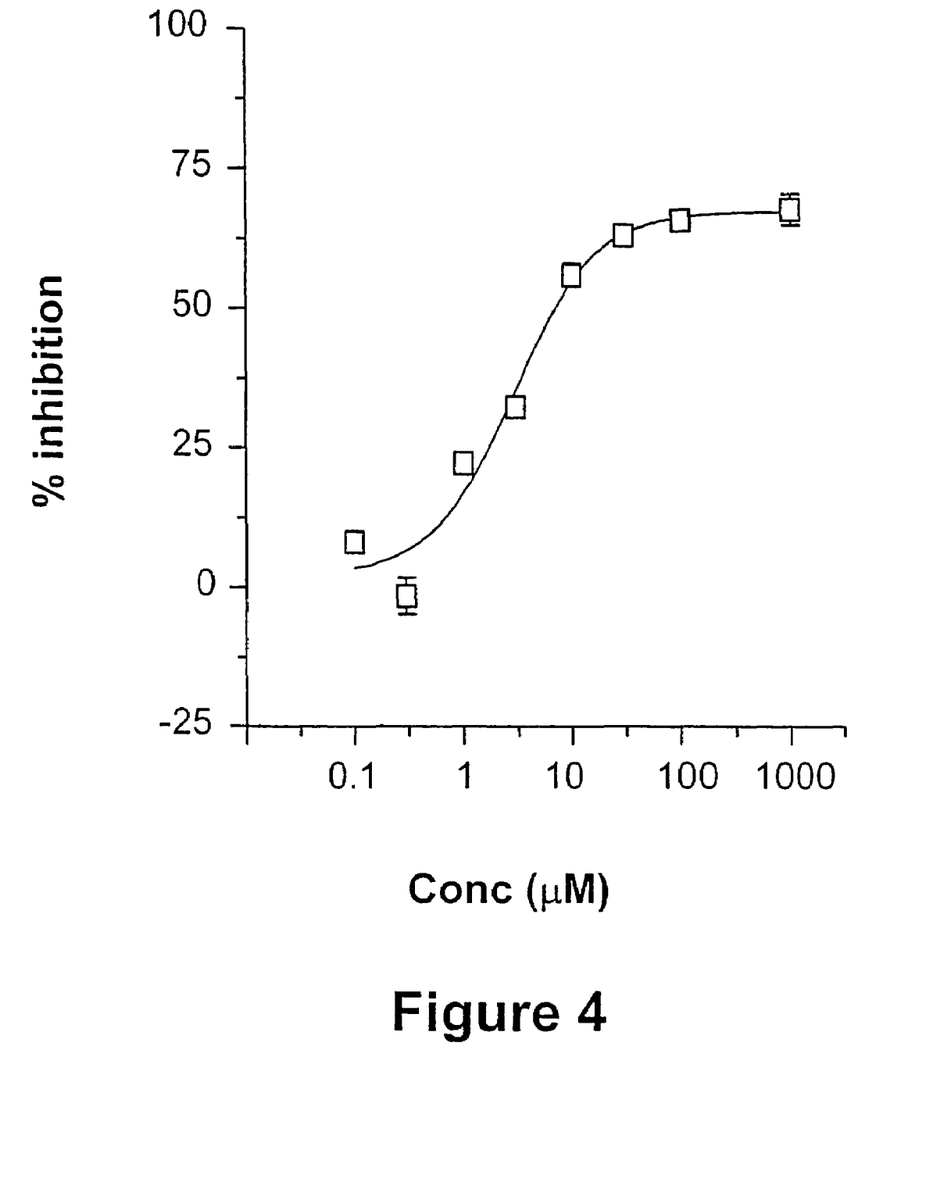
FIG. 4 is a graph showing the percentage inhibition of transpeptidase (and thus peptidoglycan synthesis) versus penicillin concentration (after subtracting the corresponding 0% reaction readings).
Figure 5:
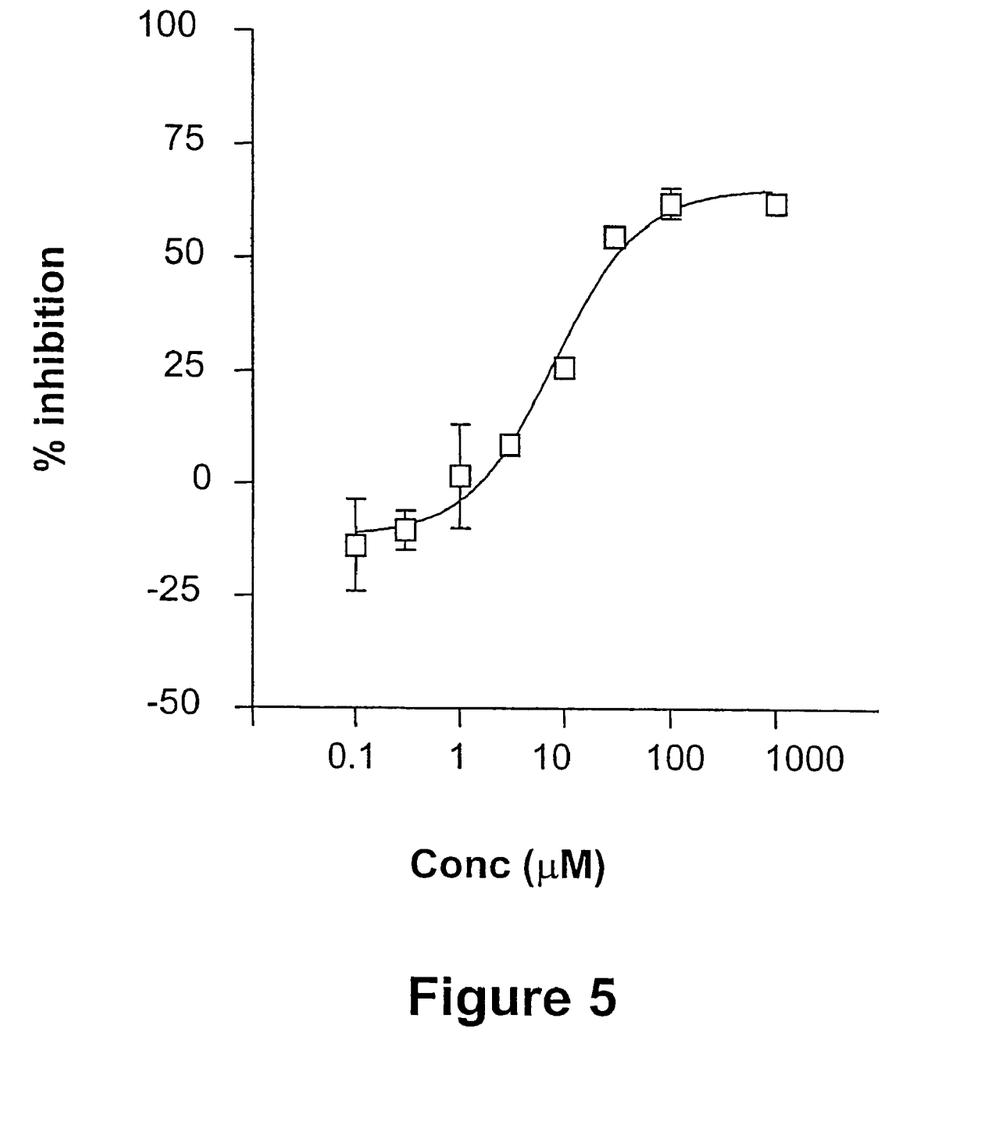
FIG. 5 is a graph showing the percentage inhibition of transpeptidase (and thus peptidoglycan synthesis) versus ampicillin concentration (after subtracting the corresponding 0% reaction readings).

The results are shown in FIG. 1.

EXAMPLE 2

The method described in Example 1 was repeated except that in (i) the membranes used were those of an *Escherichia coli* mutant, AMA1004 ΔponB::Spc$^r$, a mutant from which the gene ponB encoding PBP1b has been inactivated, as described by S. Y. Yousif, J. K. Broome-Smith and B. G. Spratt, *J. Gen. Microbiol.*, (1985), 131, 2839-2845. These membranes lacked PBP1b activity which is the major transglycosylase in *Escherichia coli* and thus there was no need to add any vancomycin inhibitor.

In (ii), the tripeptide was replaced by an extract containing PBP1b, a source of transglycosylase and transpeptidase enzymes, obtained from the membranes of *Escherichia coli* AMA1004 ΔponA; pBS96. In this strain of *E. coli*, the ponA gene encoding PBP1a is inactivated and the ponB gene encoding PBP1b is overexpressed since the strain contains a plasmid comprising a further copy of ponB under the control of its native promoter.

The membranes of this *E. coli* strain were prepared as described in WO 99/60155. They were then treated with a detergent, 1% w/v 3-[(3-cholamidopropyl)dimethylammonio]-1-propane-sulphonate (CHAPS), and 1M NaCl at a protein concentration of 5 mg/ml for 1 hour at room temperature. The mixture was then centrifuged at 150,000×g for 15 minutes in a Beckman table top ultracentrifuge and the supernatant containing PBP1b collected. The quantity of PBP1b protein used was the "soluble fraction" equivalent to 0.75 µg of starting membrane and an excess of 1% w/v CHAPS, 1M NaCl solution was added such that the final concentration (in 25 µl) was 0.04% v/v CHAPS, 40 mM NaCl.

Four test compounds were used in (ii): moenomycin, vancomycin, penicillin and ampicillin, the first two being known transglycosylase inhibitors and the second two being known transpeptidase inhibitors.

Four wells of the microtitre plate were used as controls: in two wells 1 µl of 1% w/v CHAPS, 1M NaCl was added instead of the solubilised membrane, so that the final concentration (in 25 µl) was 0.04% w/v CHAPS, 40 mM NaCl (0% reaction controls) and a further two wells contained no test compound (100% reaction controls).

The microtitre plate in (ii) was incubated at 37° C. for 20 minutes before addition of the EDTA.

The results are shown in FIGS. 2, 3, 4 and 5.

EXAMPLE 3

(i) Formation of Radiolabelled Lipid II

The wells of a microtitre plate are individually filled with a total volume of 15 µl of a solution containing 4 µg cell membranes of *Escherichia coli* mutant, AMA1004 ΔponB::Spc$^r$ when transformed with a plasmid comprising either the ponA gene and expressing PBP1a or the ponB gene and expressing PBP1b, 40 µM vancomycin, 15 µM UDP-MurNAc-L-alanine-γ-D-glutamic acid-m-diaminopimelic acid-D-alanine-D-alanine, 2.5 µM tritiated UDP-N-acetyl glucosamine (0.1 µCi per well), 50 mM HEPES-ammonia buffer pH 7.5, and 10 mM magnesium chloride (MgCl$_2$).

The microtitre plate is incubated at 37° C. for 120 minutes.

(ii) Formation of Radiolabelled Peptidoglycan

To each well is then added 10 µl containing 50 mM HEPES-ammonia buffer pH 7.5, 10 mM MgCl$_2$, UDP-N-acetyl glucosamine to a final concentration (in 25 µl) of 250 µM, a tripeptide to neutralise the vancomycin inhibitor: NαNε, diacetyl-Lys-D-Ala-D-Ala to a final concentration of 400 µM (in 25 µl; available from Sigma-Aldrich Company, catalogue number D-9904), and 2 µl of test compound in dimethyl sulphoxide (DMSO).

The microtitre plate is then incubated at 37° C. for 5 minutes and thereafter 75 µl of 6 mM ethylenediaminetetraacetic acid (EDTA) is added to stop any further peptidoglycan synthesis.

(iii) Detecting Radiolabelled Peptidoglycan

Following addition of the EDTA, there is added to each well 100 µl of an aqueous suspension of wheatgerm agglutinin-coated scintillation proximity assay beads comprising 500 µg beads in a solution of 50 mM HEPES-ammonia buffer pH 7.5 containing 0.4% "Sarkosyl" detergent (sodium lauryl sarcosinate) so that the final concentration of "Sarkosyl" detergent (in 200 µl) is 0.2%.

The microtitre plate is left for 3 to 10 hours at room temperature before being counted in the "Microbeta Trilux" counter.

Four wells of the microtitre plate are used as controls: two wells have EDTA and 10 µl water added at the end of (i) (0% reaction controls) and a further two wells contain no test compound (100% reaction controls).

What is claimed is:

1. A method of screening for potential anti-bacterial agents which comprises:
    (1) providing a membrane preparation obtained from a bacterial strain that is deficient for peptidoglycan transglycosylase activity;
    (2) preparing a reaction mixture comprising the membrane preparation, a UDP-N-acetylmuramylpentapeptide, radiolabelled UDP-N-acetyl glucosamine and a source of divalent metal ions;
    (3) incubating the reaction mixture for a defined period under conditions suitable for Lipid II synthesis to occur;
    (4) adding to the reaction mixture of step (3),
        (a) a source of peptidoglycan transglycosylase and a source of peptidoglycan transpeptidase, to allow further processing of Lipid II formed in step (3) toward peptidoglycan, and
        (b) a test compound;
    (5) after a defined period, terminating any further processing of Lipid II;
    (6) adding to the reaction mixture of step (5) a fluorescer supported, by in or on a suitable substrate, and a detergent; and
    (7) measuring light energy emitted by the fluorescer which is indicative of the presence of radiolabelled peptidoglycan, wherein a decrease in light energy emitted by the fluorescer in the presence of the test compound as compared to a control with no compound is indicative that the test compound is a potential anti-bacterial agent.

2. The method according to claim 1, wherein the UDP-N-acetylmuramylpentapeptide is UDP-MurNAc-L-alanine-γ-D-glutamic acid-m-diaminopimelic acid-D-alanine-D-alanine.

3. The method according to claim 1, wherein the source of divalent metal ions is magnesium chloride.

4. The method according to claim 1 wherein the bacterial strain is a strain of *Escherichia coli*.

5. The method according to claim 4, wherein the *Escherichia coli* strain is AMA1004 ΔponB::Spc$^r$.

6. The method according to claim 1, wherein the fluorescer is supported by, in or on lectin-coated beads.

7. The method according to claim 1, wherein the test compound is an antagonist of one or both of the transglycosylase and the transpeptidase.

8. The method according to claim 1, wherein the detergent is selected from t-octylphenoxypolyethoxyethanol and sodium lauryl sarcosinate.

* * * * *